(12) United States Patent
Huffstodt et al.

(10) Patent No.: US 8,465,696 B2
(45) Date of Patent: Jun. 18, 2013

(54) DRY TEST STRIP WITH CONTROLLED FLOW AND METHOD OF MANUFACTURING SAME

(75) Inventors: Robert Huffstodt, Indianapolis, IN (US); John P. Hancock, Fishers, IN (US); Emmanuel Paul Crabtree, Crossville, TN (US); James J. Sutor, Greenwood, IN (US); Kimberly Zinser Huffstodt, Indianapolis, IN (US); Gregory M. Lawrence, Indianapolis, IN (US)

(73) Assignee: Polymer Technology Systems, Inc., Indianapolis, IN (US)

( * ) Notice: Subject to any disclaimer, the term of this patent is extended or adjusted under 35 U.S.C. 154(b) by 1029 days.

(21) Appl. No.: 11/933,292

(22) Filed: Oct. 31, 2007

(65) Prior Publication Data

US 2008/0112848 A1 May 15, 2008

Related U.S. Application Data

(63) Continuation-in-part of application No. 11/207,121, filed on Aug. 17, 2005, which is a continuation-in-part of application No. 10/962,272, filed on Oct. 11, 2004, now Pat. No. 7,435,577.

(60) Provisional application No. 60/602,210, filed on Aug. 17, 2004, provisional application No. 60/541,681, filed on Feb. 3, 2004.

(51) Int. Cl.
*G01N 15/06* (2006.01)

(52) U.S. Cl.
USPC .................................................. 422/68.1

(58) Field of Classification Search
USPC .................................................. 422/68.1
See application file for complete search history.

(56) References Cited

U.S. PATENT DOCUMENTS

| 4,319,008 | A | 3/1982 | Marze et al. |
| 4,362,078 | A | 12/1982 | Ohnishi et al. |
| 4,477,575 | A | 10/1984 | Vogel et al. |

(Continued)

FOREIGN PATENT DOCUMENTS

WO    WO-03/058252 A2    7/2003

OTHER PUBLICATIONS

In the US Patent and Trademark Office U.S. Appl. No. 10/962,272, Final Office Action dated Aug. 17, 2007, 8 pages.

(Continued)

*Primary Examiner* — Lore Jarrett
(74) *Attorney, Agent, or Firm* — Patton Boggs LLP

(57) ABSTRACT

A dry test strip assembly includes: a carrier base having a test port and a well adapted for receiving a dry test strip element, and a cover having a sample opening. The cover can be snapped onto the base with the sample opening aligned over the test port and with a test strip element compressed between the base and cover. A maximum dry test strip compression stop controls the maximum compression on the dry test strip, and a minimum dry test strip compression stop controls the minimum compression on the dry test strip. A rib between two test ports prevents fluid flow in the dry test strip element from one side of the rib to another, thereby separating the test strip element into a plurality of separate fluid compartments. A manufacturing system efficiently assembles the dry test strip assembly without handling by humans.

1 Claim, 13 Drawing Sheets

U.S. PATENT DOCUMENTS

| | | | |
|---|---|---|---|
| 4,549,655 A * | 10/1985 | Forsythe et al. | 206/569 |
| 4,774,192 A | 9/1988 | Terminiello et al. | |
| 4,780,411 A | 10/1988 | Piejko et al. | |
| 4,916,056 A | 4/1990 | Brown, III et al. | |
| 4,943,522 A | 7/1990 | Eisinger et al. | |
| 4,987,085 A | 1/1991 | Allen et al. | |
| 5,013,339 A | 5/1991 | Mahoney et al. | |
| 5,104,619 A | 4/1992 | de Castro et al. | |
| 5,145,583 A | 9/1992 | Angleraud et al. | |
| 5,166,051 A | 11/1992 | Killeen et al. | |
| 5,212,060 A | 5/1993 | Maddox | |
| 5,240,862 A | 8/1993 | Koenhen et al. | |
| 5,389,338 A * | 2/1995 | Fish | 422/401 |
| 5,580,744 A | 12/1996 | Zweig | |
| 5,597,532 A | 1/1997 | Connolly | |
| 5,676,032 A | 10/1997 | Johnson | |
| 5,695,947 A | 12/1997 | Guo et al. | |
| 5,753,497 A | 5/1998 | Bernstein et al. | |
| 6,008,059 A | 12/1999 | Schrier et al. | |
| 6,040,195 A | 3/2000 | Carroll et al. | |
| 6,130,100 A | 10/2000 | Jobling et al. | |
| 6,162,397 A | 12/2000 | Jurik et al. | |
| 6,287,867 B1 | 9/2001 | Harttig et al. | |
| 6,340,589 B1 * | 1/2002 | Turner et al. | 435/287.2 |
| 6,440,306 B1 | 8/2002 | Ditter et al. | |
| 6,488,828 B1 | 12/2002 | Bhullar et al. | |
| 6,699,720 B1 | 3/2004 | Lee et al. | |
| 6,939,468 B2 | 9/2005 | Wang et al. | |
| 7,135,150 B2 | 11/2006 | Noda | |
| 7,435,577 B2 | 10/2008 | Lawrence et al. | |
| 2001/0005488 A1 | 6/2001 | Hirao et al. | |
| 2002/0043095 A1 | 4/2002 | Mason et al. | |
| 2003/0143523 A1 | 7/2003 | Kato et al. | |
| 2003/0175153 A1 | 9/2003 | Anaokar et al. | |
| 2004/0126830 A1 * | 7/2004 | Shull et al. | 435/11 |
| 2004/0167237 A1 | 8/2004 | Kim et al. | |
| 2006/0062688 A1 | 3/2006 | Lawrence | |
| 2006/0188392 A1 | 8/2006 | Tanaka et al. | |

OTHER PUBLICATIONS

In the US Patent and Trademark Office U.S. Appl. No. 10/962,272, Non-Final Office Action dated Feb. 25, 2008, 6 pages.

In the US Patent and Trademark Office U.S. Appl. No. 10/962,272, Non-Final Office Action dated Mar. 5, 2007, 8 pages.

In the US Patent and Trademark Office U.S. Appl. No. 11/206,590, Advisory Action dated Jul. 13, 2009, 3 pages.

In the US Patent and Trademark Office U.S. Appl. No. 11/206,590, Final Office Action dated Apr. 15, 2009, 6 pages.

In the US Patent and Trademark Office U.S. Appl. No. 11/206,590, Final Office Action dated Feb. 3, 2010, 7 pages.

In the US Patent and Trademark Office U.S. Appl. No. 11/206,590, Non-Final Office Action dated Aug. 29, 2008, 5 pages.

In the US Patent and Trademark Office U.S. Appl. No. 11/206,590, Non-Final Office Action dated Sep. 29, 2009, 7 pages.

In the US Patent and Trademark Office U.S. Appl. No. 11/206,893, Non-Final Office Action dated Feb. 18, 2009, 7 pages.

In the US Patent and Trademark Office U.S. Appl. No. 11/207,121, Final Office Action dated Dec. 24, 2008, 16 pages.

In the US Patent and Trademark Office U.S. Appl. No. 11/207,121, Final Office Action dated Mar. 9, 2011, 12 pages.

In the US Patent and Trademark Office U.S. Appl. No. 11/207,121, Final Office Action dated Nov. 27, 2009, 16 pages.

In the US Patent and Trademark Office U.S. Appl. No. 11/207,121, Non-Final Office Action dated Apr. 27, 2009, 17 pages.

In the US Patent and Trademark Office U.S. Appl. No. 11/207,121, Non-Final Office Action dated Feb. 13, 2008, 11 pages.

In the US Patent and Trademark Office U.S. Appl. No. 11/207,121, Non-Final Office Action dated Jul. 27, 2012, 15 pages.

In the US Patent and Trademark Office U.S. Appl. No. 11/207,121, Non-Final Office Action dated Jun. 20, 2008, 14 pages.

In the US Patent and Trademark Office U.S. Appl. No. 12/580,866 Final Office Action dated Feb. 14, 2012, 7 pages.

In the US Patent and Trademark Office U.S. Appl. No. 12/580,866 Non-Final Office Action dated Aug. 11, 2011, 8 pages.

In the US Patent and Trademark Office U.S. Appl. No. 12/772,707 Non-Final Office Action dated May 29, 2012, 8 pages.

Arfors et al.; "Pharmacological characteristics of artificial colloids," *Baillière's Clinical Anaesthesiology*, 1997; 11(1):15-47.

Feng et al.; "Adsorption of High Density Lipoproteins (HDL) on Solid Surfaces"; Journal of Colloid and Interface Science; 1996; vol. 177; pp. 364-371.

Santee; "Accuracy and precision of the Cholestech LDX System in monitoring blood lipid levels"; American Journal of Health-System Pharmacy; 2002; vol. 59; pp. 1774-1779.

Sigiuchi et al.; "Direct Measurement of High-Density Lipoprotein Cholesterol in Serum with Polyethylene Glycol-Modified Enzymes and Sulfated α-Cyclodextrin"; Clinical Chemistry; 1995; vol. 41, No. 5; pp. 717-723.

Sugiuchi et al.; "Homogeneous assay for measuring low-density lipoprotein cholesterol in serum with triblock copolymer and α-cyclodextrin sulfate," *Clinical Chemistry*, 1998; 44(3):522-531).

* cited by examiner

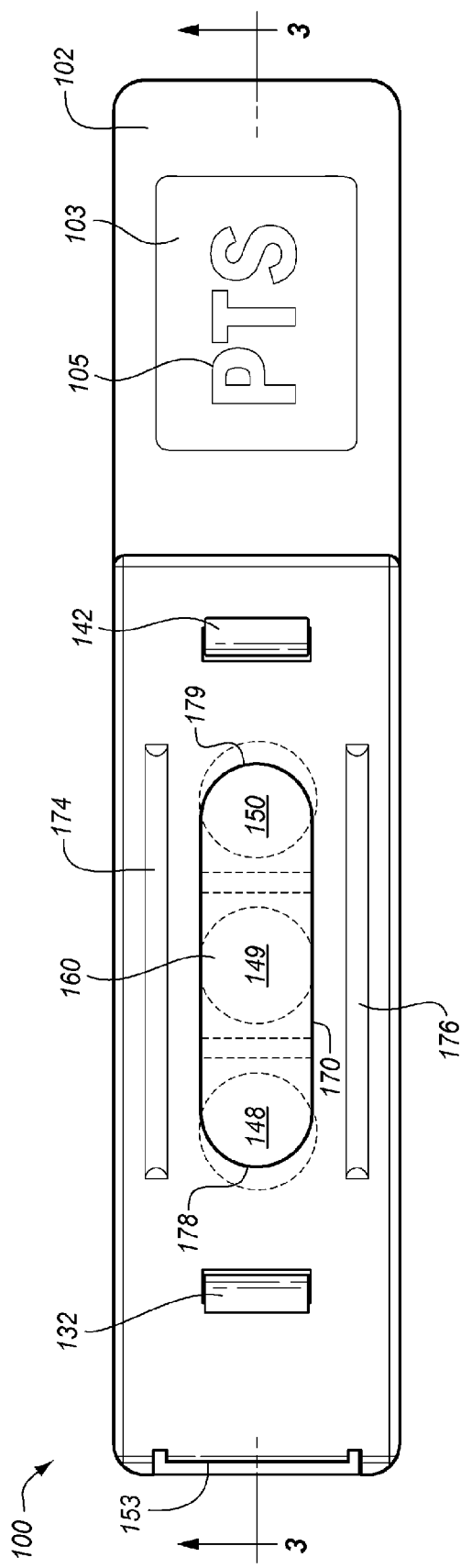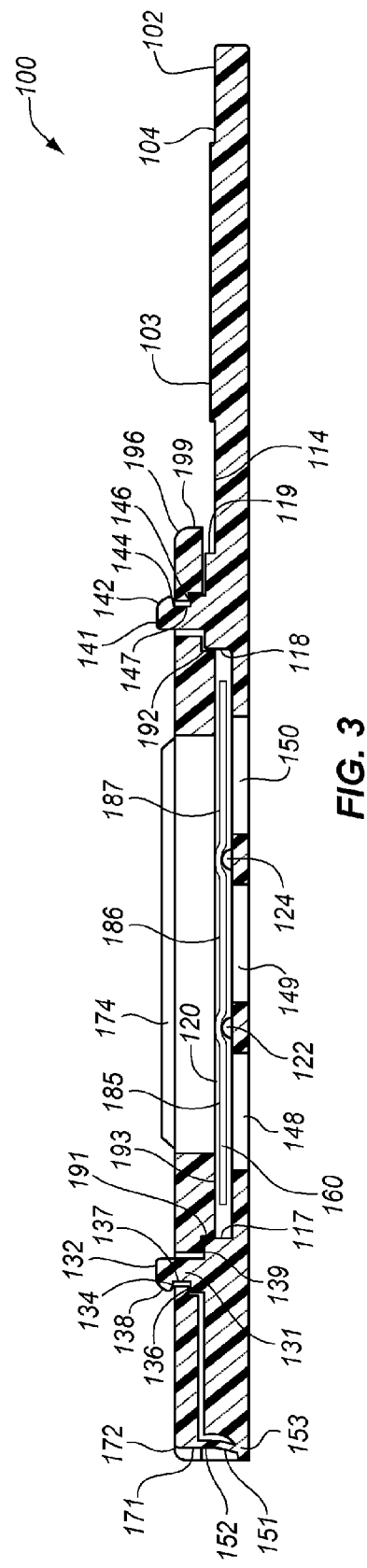

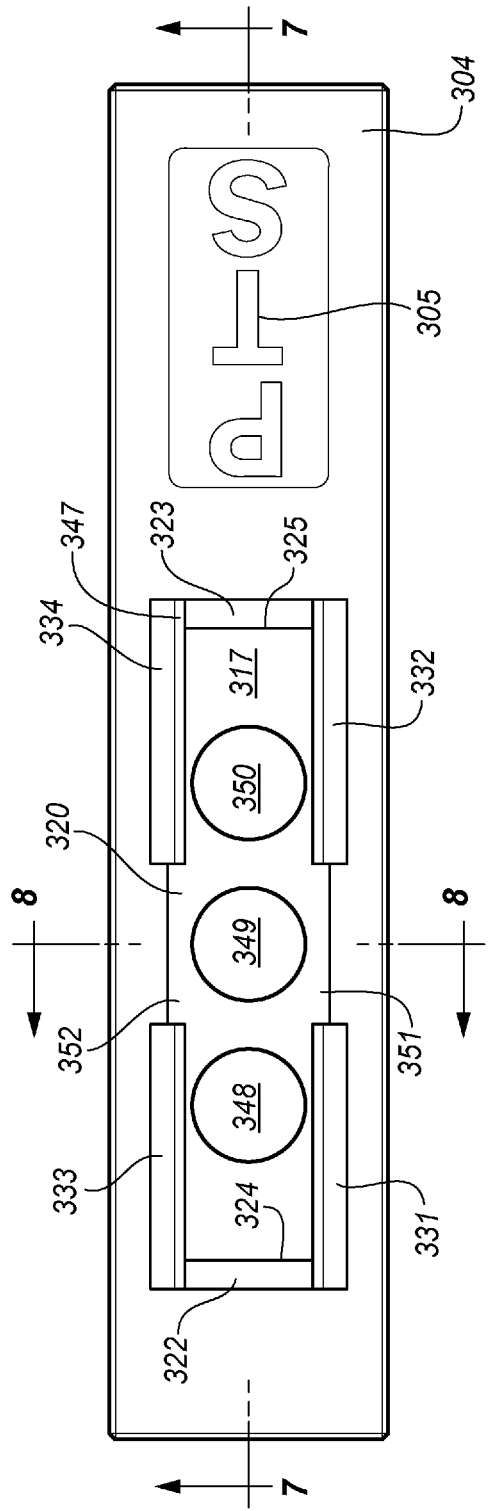
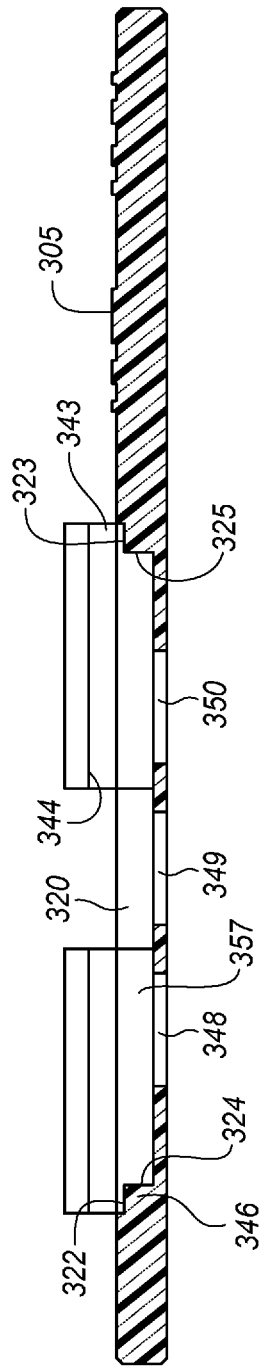
FIG. 6
FIG. 7

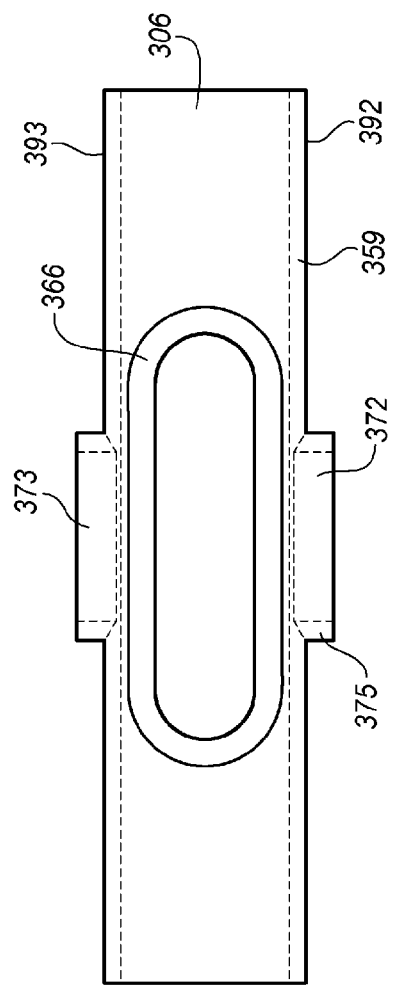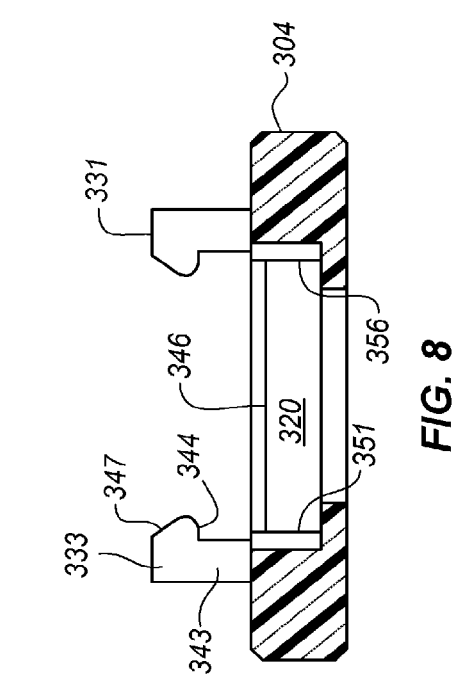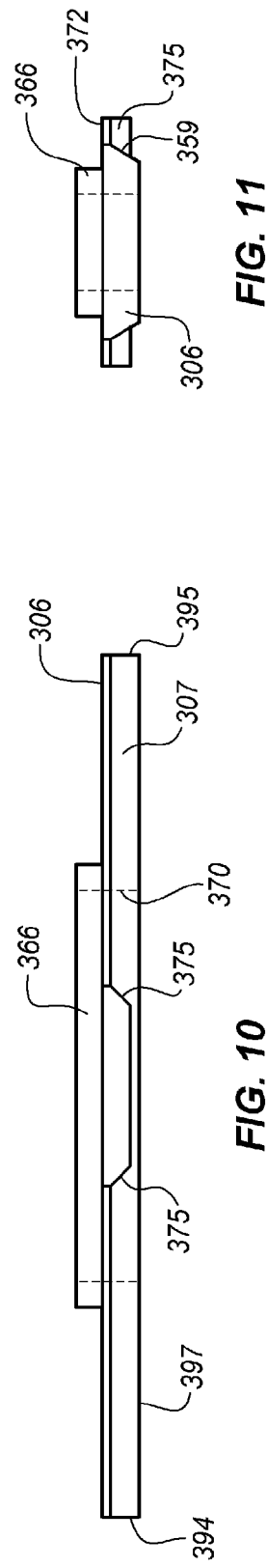

DRY TEST STRIP WITH CONTROLLED FLOW AND METHOD OF MANUFACTURING SAME

CROSS-REFERENCE TO RELATED APPLICATIONS

This application is a continuation-in-part of U.S. patent application Ser. No. 11/207,121 filed Aug. 17, 2005, which itself is a continuation-in-part of U.S. patent application Ser. No. 10/962,272 filed Oct. 11, 2004, which claims the benefit of U.S. Provisional Application No. 60/541,681 filed Feb. 3, 2004. U.S. patent application Ser. No. 11/207,121 also claims the benefit of U.S. Provisional Application No. 60/602,210 filed Aug. 17, 2004. All of the above patent applications, both provisional and non-provisional, are hereby incorporated by reference to the same extent as though fully contained herein.

FIELD OF THE INVENTION

The invention in general relates to bodily fluid analysis systems including a disposable test strip, with particular application to on-site testing of particular analytes in blood.

BACKGROUND OF THE INVENTION

The level of certain analytes in blood and other body fluids is often used to diagnose disease, determine disease risk factors, monitor the course of a therapy, or determine the presence of illicit drugs. In recent years, analytes carried in blood have been evaluated to determine various cholesterol and triglyceride levels as a significant indicator of risk of coronary heart disease. In managing heart disease, physicians commonly order what is referred to in the art as a "full lipid panel" for patients to determine the concentration of total cholesterol, high density lipoprotein cholesterol (HDL), low density lipoprotein cholesterol LDL), and triglycerides. Glucose and ketone dry test strips are used for managing diabetes. Ketone test strips also are useful in managing weight loss. Test strips for determining creatinine concentration in the blood or other bodily fluids are used for diagnosing and treating impaired kidney function and a variety of other metabolic disorders and diseases.

While clinical tests have been used and still are being used to determine the concentration of the above-mentioned analytes, more and more physicians and consumers are relying on dry test strips for economical and easier measurement, particularly when testing at shorter intervals, such as days or weeks, is important or when rapid results are critical.

The dry test strip assembly includes a dry test strip carrier and a fluid permeable strip. The dry test strip carrier generally is made of a plastic having a tensile strength of about 4,800 pounds per square inch (psi). The permeable strip includes several layers of material to separate the blood components, react the blood plasma with a particular reagent or reagents, and obtain a signal indicative of the concentration of the analyte. See, for example, U.S. Pat. No. 5,104,619 issued Apr. 14, 1992 to de Castro et al. and entitled "Disposable Diagnostic System"; U.S. Pat. No. 5,166,051 issued Nov. 24, 1992 to Killen et al. and entitled "Membranes, Membrane Overlays, For Exclusion of Erythrocytes, And Method Of Immunoassay of Whole Blood Analytes"; U.S. Pat. No. 4,774,192 issued to Terminello et al. on Sep. 27, 1988 and entitled "A Dry Reagent Delivery System With Membrane Having Porosity Gradient"; and U.S. Pat. No. 4,477,575 issued to Vogel et al. on Oct. 16, 1984 and entitled "Process And Composition For Separating Plasma Or Serum From Whole Blood". In more recent systems, the dry test strip in the strip carrier is placed within a spectrophotometric device that evaluates the colorimetric response and assigns a quantitative value indicative of the analyte concentration in the blood, urine, or other bodily fluid sample. For example, see U.S. Pat. No. 5,597,532 issued to James Connolly on Jan. 28, 1997, owned by the assignee of the present invention, and entitled "Apparatus For Determining Substances Contained In A Body Fluid", which patent is incorporated by reference to the same extent as though fully disclosed herein. Most modern dry test strip assemblies follow the teachings of the Connolly patent, utilizing a carrier comprising a base and a cover, with the fluid permeable strip held between the base and cover.

All of the above systems depend on the flow of the bodily fluid, i.e., blood, through the system as the driving force to separate the unwanted components from the components to be tested. The red blood cells are separated from the serum, and the analyte to be tested is isolated from the other components: in a system for testing HDL, for example, the lipoproteins other than HDL are isolated from the HDL. Thus, the control of the flow is important for the tests to be accurate. For example, U.S. Pat. No. 4,774,192 relies on a highly porous bottom layer to allow the fluid to flow easily and a dense upper layer to trap the unwanted components. In U.S. Pat. No. 4,477,575, a lateral flow of blood through a fiberglass layer is used to separate the components. U.S. Pat. No. 5,597,532 uses a vertical flow downward through membranes and a lateral flow outward in a lower membrane that is designed to absorb a large amount of fluid to drive the fluid flow. A rectangular test membrane that is significantly larger than the area of the circular opening through which a spectrophotometer reads the strip enhances this feature to encourage flow and prevent blood pooling in the test area of the membrane. These flow properties are determined by the permeable materials from which the strip material is made and by the carrier for the strip. If the strip is held loosely in the carrier, flow is augmented, but the strip can move, which can lead to erroneous results. If the strip is held firmly, damage can result, which leads to erratic results as well as inaccuracies. Thus, test strip carriers have been designed that permit vertical and lateral flow through most of the strip, but tightly hold other parts of the strip. See, for example, U.S. Pat. No. 5,597,532 referenced above. However, the accuracies of test strips still remain lower than similar tests performed in the laboratory.

The design of dry test strips and carriers also is constrained by the need to manufacture the strip. The strip and carrier should be able to be manufactured and assembled quickly but without negatively affecting the reliability and accuracy of the strip. Up until now, final automated systems used up several times the amount of fluid permeable strip than was required for the strips themselves, which was costly. To efficiently use the strip, the final assembly was by hand. This hand labor adds to the cost of the system.

It would be highly desirable to have a test strip system that improved the accuracy of the tests, but at the same time could be more economically manufactured, particularly one in which the hand labor was minimized without excessive use of strip material and without compromising the reliability and accuracy of the system.

BRIEF SUMMARY OF THE INVENTION

The present invention provides a solution to the above problems by providing a dry test strip carrier system in which the compression the carrier applies to a strip is accurately controlled. The accurate control of the compression permits more accurate control of the flow of the fluid through the strip and, thus, improves the repeatability and accuracy of the test. The compression is controlled with parameters to provide consistent flow from one test strip to another. The accuracy of the test in part is determined by the repeatability of the flow from test trip to test strip, both with respect to the timing of the flow through the strip from top to bottom and the path the flow takes. In the preferred embodiment, the carrier controls the flow to provide a plurality of flow paths in a continuous strip. The structure provides separate fluid-tight compartments in a single continuous strip. This yields a multi-analyte test strip that is much simpler to assemble.

The amount of compressive force is controlled by controlling the vertical position of the cover with respect to the base with a pair of stops. A maximum dry test compression stop controls the maximum compression of the dry test strip, and a minimum dry test strip compression stop controls the minimum compression of the dry test strip. Preferably, there are first and second maximum compression stops and first and second minimum compression stops. The flexibility of the cover and base are also controlled, particularly between the first and second stops. The base and a cover snap together, which also simplifies the assembly.

The accuracy of the strip is also improved by controlling the horizontal position of the dry test strip within the carrier. In the preferred embodiment, the base of the carrier includes a dry test strip well, and the dry test strip is held within the well.

The foregoing features of the dry test strip assembly allow, for the first time, a dry test strip assembly that can be assembled automatically by machinery without excess use of permeable strip material or human handling. A dry test strip assembly manufacturing system is also provided by the invention.

The invention provides a carrier system for a diagnostic dry test strip for use in measuring an analyte in a fluid sample, the carrier system comprising: a carrier base including a test strip well adapted for receiving a dry test strip and a test port communicating with the well and enabling the test strip to be observed; a cover having a sample opening; and engagement elements on the carrier base and the cover configured to engage the cover to the carrier body with the sample opening aligned over the test port and the dry test strip compressed between the carrier base and the cover; wherein the engagement elements include: a maximum dry test strip compression stop controlling the maximum compression on the dry test strip; and a minimum dry test strip compression stop controlling the minimum compression on the dry test strip. Preferably, the maximum dry test strip compression stop comprises a landing pad formed on the base or cover and adapted to contact a portion of the other of the base or cover. Preferably, the engagement elements include a snap-on latch, and the minimum dry test strip compression stop comprises a lip on the latch. Preferably, the carrier system includes a proximal end adapted to be grasped by a human hand and a distal end adapted to be inserted into an analyzer, the cover is attached to the base near the distal end by a living hinge, and the engagement elements include a snap-on latch. Preferably, the cover is made of glass-filled polypropylene. Preferably, the cover has a tensile strength of between 10,000 pounds per square inch (psi) and 14,000 psi.

In another aspect, the invention provides a carrier system for a diagnostic dry test strip for use in measuring an analyte in a fluid sample, the carrier system comprising: a carrier having a proximal end adapted to be grasped with human fingers and a distal end adapted to be inserted into an analyzer; the carrier comprising a carrier base and a carrier cover connected by a hinge located near the distal end of the carrier; the carrier base including a test port and the carrier cover including a sample opening, with the sample opening aligned over the test port when the cover is closed over the base; wherein the hinge attaches to at least one of the base and cover at a location recessed from the distal end of the carrier. Preferably, the hinge is a living hinge. Preferably, the hinge is a double living hinge.

In a further aspect, the invention provides a multi-analyte diagnostic dry test strip system, the dry test strip system comprising: a carrier base including a plurality of test ports and a carrier cover including one or more sample openings, with the one or more sample openings aligned over the test ports when the cover is closed over the base; and a dry test strip compressed between the base and cover and extending continuously over a plurality of the test ports; wherein at least one of the base and cover includes a raised rib located between two of the test ports and adapted to compress the dry test strip sufficiently so that essentially no fluid can flow in the dry test strip from one side of the rib to another, thereby separating the continuous dry test strip into a plurality of separate fluid compartments. Preferably, there are three of the test ports spaced apart longitudinally on the base and two of the ribs, each rib located between the center one of the test ports and one of the end ones of the test ports. Preferably, the ribs extend between 0.014 inches and 0.035 inches in height from the surface of the base. More preferably, the ribs extend between 0.020 inches and 0.030 inches in height from the surface of the base. Preferably, the carrier cover is made of glass-filled polypropylene. Preferably, the polypropylene is 30% glass-filled polypropylene. Preferably, the carrier cover has a tensile strength between 10,000 psi and 14,000 psi.

The invention also provides a method of assembling a dry test strip assembly having a plurality of separate fluid compartments, the method comprising: placing a continuous dry test strip element on a dry test strip carrier base having first and second test ports, the continuous dry test strip material covering the first and second test ports and having a first test strip element portion over the first test port and a second test strip element portion over the second test port; and the continuous dry test strip element having reagent layers having essentially no breaks between the first and second test strip element portions of the reagent layers; and snapping a cover on the base while sufficiently compressing the dry test strip element between the cover and the base at a location between the first and second test ports so that fluid cannot flow between the first test strip element portion and the second test strip element portion, thereby dividing the continuous dry test strip into the plurality of separate fluid compartments.

In yet another aspect, the invention provides a method of manufacturing a dry test strip assembly, the method comprising: placing a dry test strip carrier base on a conveyer, the base having a well; conveying the test strip carrier base on the conveyer to a cutting station and then to a cover station; at the cutting station, cutting a dry test strip element from a dry test strip material, and placing the cut dry strip element in the well in the base; at the cover station, snapping a cover onto the base, thereby compressing the dry test strip element between the cover and the base to complete the dry test strip assembly; wherein the placing, conveying, cutting, and snapping are all performed automatically by machinery without human handling. Preferably, the cutting comprises punching out or shearing the dry test strip element from a sheet of material or a ribbon of material. Preferably, the method further comprises loading a plurality of the dry test strips in a vial and capping the vial, wherein the loading and capping are also performed automatically by machinery without human handling.

The invention provides a carrier for a diagnostic test strip in which the accuracy of the test is improved by structure that also allows the strip to be assembled by machinery. These and other objects and benefits of the invention will become apparent from the following written description and accompanying figures.

BRIEF DESCRIPTION OF THE DRAWINGS

FIG. 2 is a top view of a dry test strip assembly employing the carrier of FIG. 1;

FIG. 3 is a sectional view of the dry test strip assembly of FIG. 2;

FIG. 6 is a top plan view of the base of the carrier of the dry test strip assembly of FIG. 5;

FIG. 7 is a cross-section view of the base of the dry test strip carrier of FIG. 5 taken through the line 7-7 of FIG. 6;

FIG. 8 is a cross-section view of the base of the dry test strip carrier of FIG. 5 taken through the line 8-8 of FIG. 6;

FIG. 9 is a top plan view of the cover of the carrier of the dry test strip assembly of FIG. 5;

FIG. 10 is a side view of the cover of FIG. 9;

FIG. 11 is an end view of the cover of FIG. 9;

DETAILED DESCRIPTION OF THE INVENTION

Figure 1:
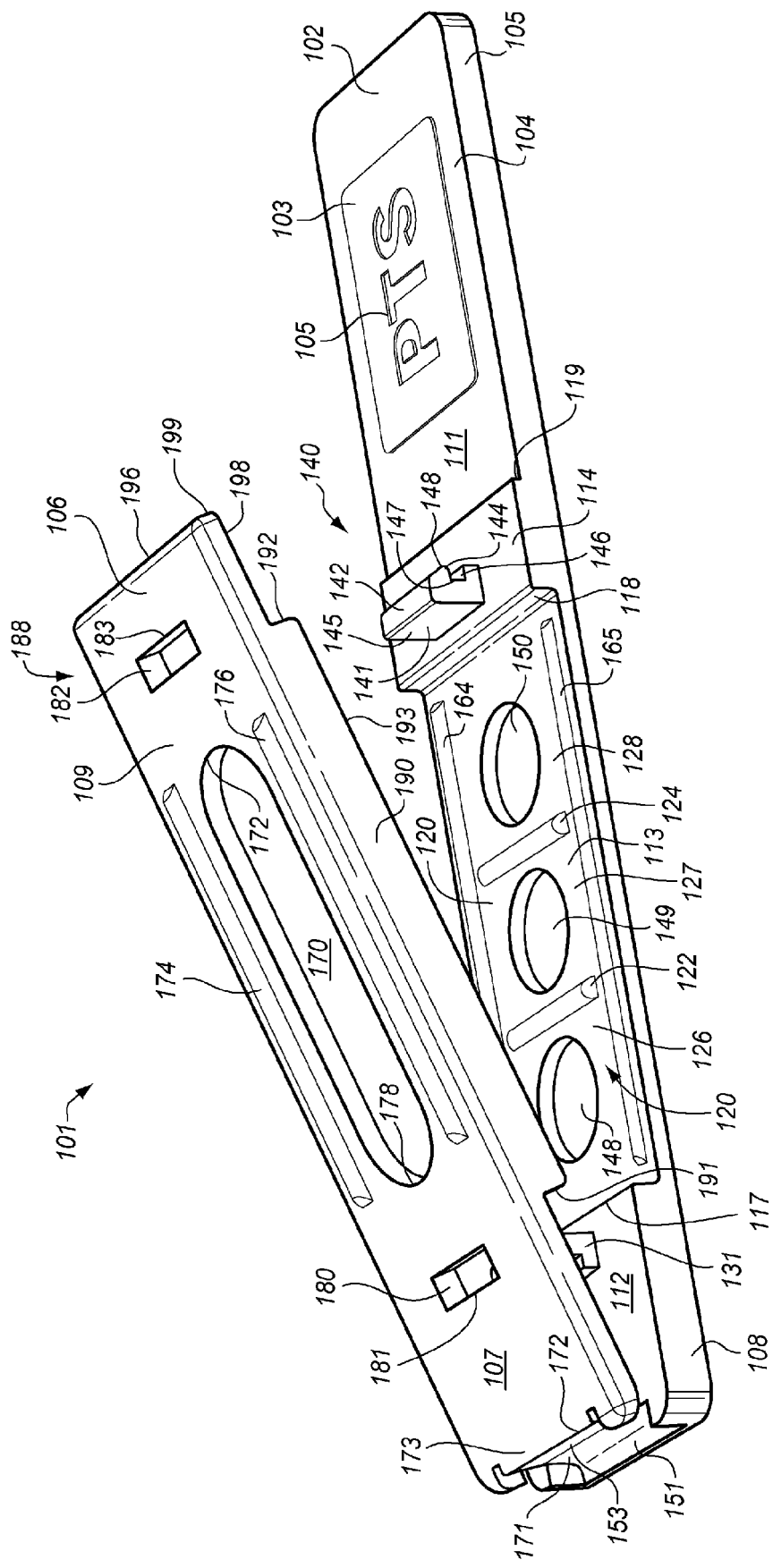
FIG. 1 is a perspective view of a preferred embodiment of a dry test strip carrier according to the invention.

For the purposes of promoting an understanding of the principles of the invention, reference will now be made to the embodiments illustrated in the drawings and described in the following written specification. It is understood that no limitation to the scope of the invention is intended thereby. It is further understood that the present invention includes any alterations and modifications to the illustrated embodiments and includes further applications of the principles of the invention as would normally occur to one skilled in the art to which this invention pertains. It should also be understood that, in accordance with the patent law, the drawings are not intended to be precise engineering drawings of the invention, but rather are only intended to illustrate the invention. For example, the scale of the drawings and relative size of the various parts are generally altered so as to better illustrate the invention within the constraints of a written document such as this.

The dry test strip assemblies according to the invention are designed for flow of the bodily fluid through the assembly under the force of gravity. The direction of flow is designated as the vertical direction herein, and the two directions perpendicular to the flow are designated as the horizontal directions herein.

Figure 12:
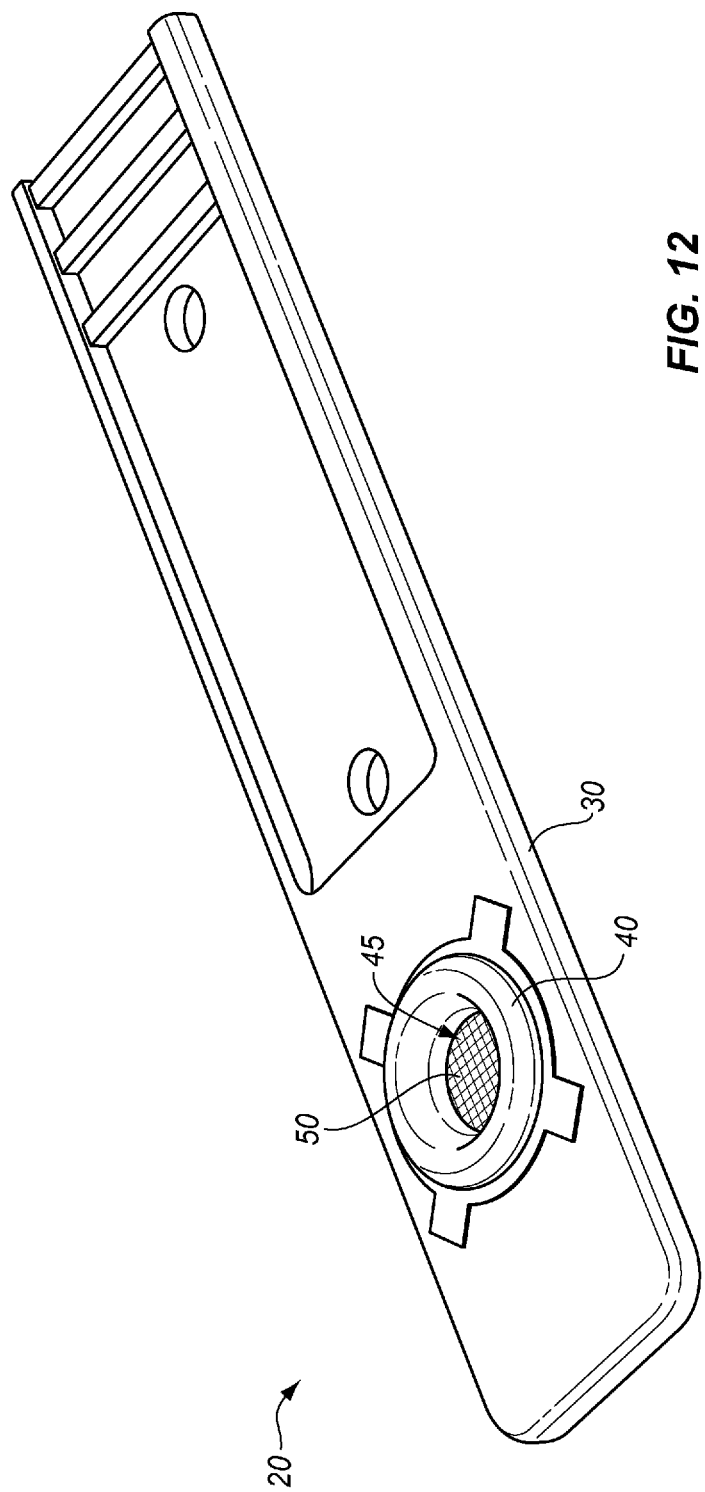
FIG. 12 is a perspective view of an alternative preferred embodiment of a test strip assembly according to the invention.

FIG. 1 shows a perspective view of a preferred embodiment of a dry test strip carrier 101 according to the invention in the open position. FIG. 2 shows a top plan view of a preferred embodiment of a dry test strip assembly 100 according to the invention, which includes dry test strip carrier 100 and fluid permeable test strip 160. Carrier 101 has a proximal end 105 and a distal end 108, and includes base 102 and cover 106. Base 102 comprises an elongated plate 104 having a raised back platform 112 and a raised forward platform 114, a depressed area 113 between them, and a tongue portion 111, which is thinner than the platforms 112 and 114. A roughened area 105, in this case in the form of the logo of the assignee, makes it easier to hold the tongue between a thumb and forefinger. Strengthening ribs 164 and 165 are formed along the side of depressed area 113. Ribs 164 and 165, together with the end walls 117 and 118 of depressed area 113, form an enclosed well 120. In this embodiment, three sensor ports 148, 149, and 150 are formed in well 120. Ribs 122 and 124, preferably spaced equidistant between the end ports 148 and 150 and the central port 149, separate well 120 into three separate test wells 126, 127, and 128. Stop members 131 and 141 are formed on platforms 112 and 114, respectively. Stop member 141 includes a pad 144 which determines the minimum distance between the base and cover and a hook-shaped end 148 forming a latch lip 144 which determines the maximum distance between the base and cover. The end 142 of stop member 141 is radiused. Stop member 131 is preferably the mirror image of stop member 141. A hinge member 151 projects from the distal end 153 of base 102. Base end 153 has an indentation 152 at hinge 151 so that, when strip assembly 10 is inserted into slot 1214 of reader 1200 (FIG. 12), base plate 104 abuts the end 1220 of slot 1214 rather than hinge 151.

Figure 20:
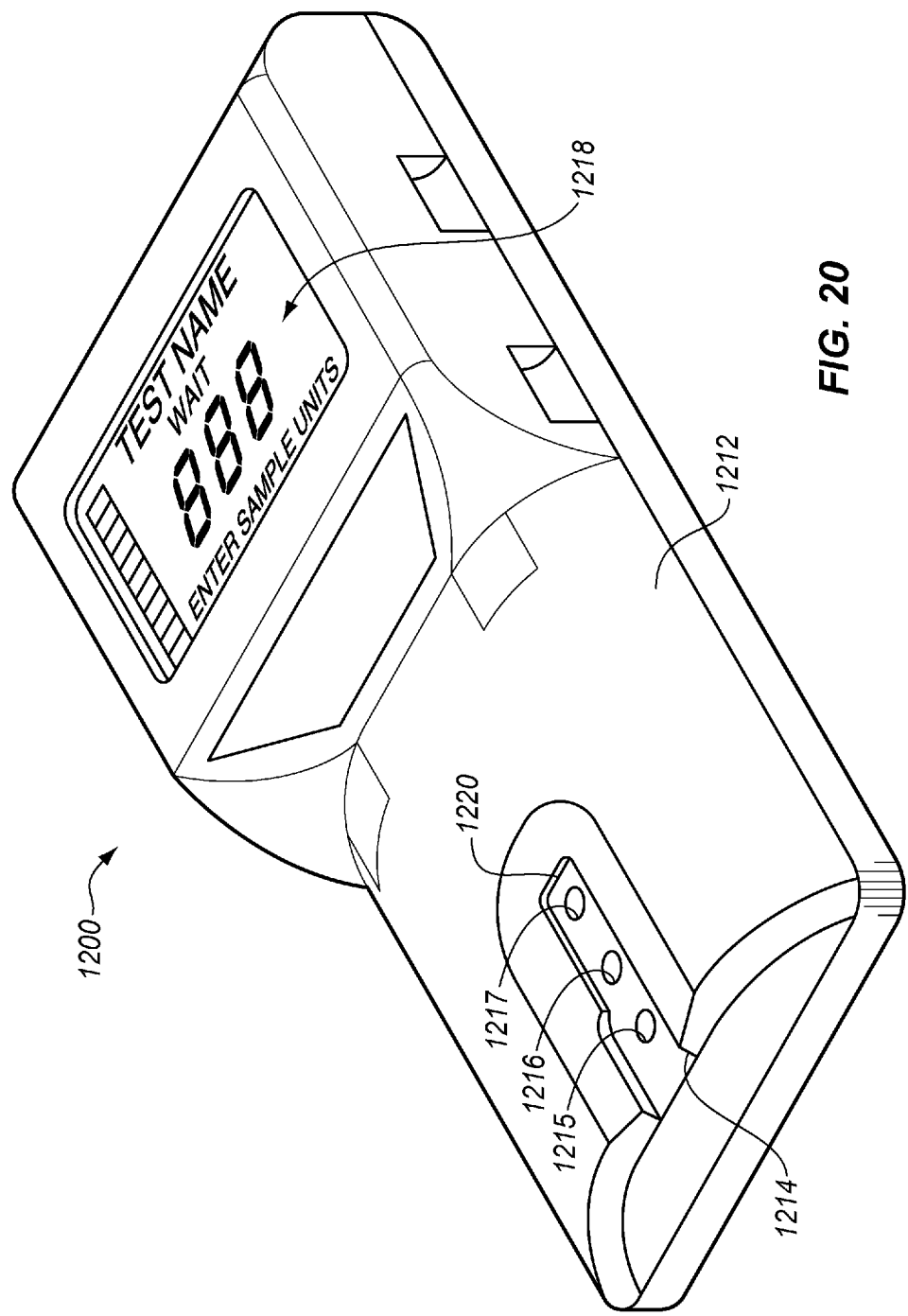
FIG. 20 is a perspective view of a preferred embodiment of a spectrophotometric device which is used to read the dry test strip assemblies according to the invention.

Cover 106 comprises an elongated plate 107 having openings 180 and 182 for receiving stop members 131 and 141, sample port 170, strengthening ribs 174, and compression plate 190 extending away from the bottom surface 198 of cover plate 107. Sample port 170 is preferably an oblong slot with semicircular ends 178 and 179, with a width that is slightly smaller than the diameter of sensor ports 148-150 and a length such that the semicircles of ends 178 and 179 lie inside the radius of the sensor ports 148 and 150. The ends 191 and 192 of compression plate 190 are formed to mesh with the ends 117 and 118 of depression 113 so that compression plate 190 fits snuggly into depression 113. Ribs 164 and 165 are preferably slightly shorter than ribs 122 and 124, so that they do not interfere with the controlled compression of dry test strip 160. A living hinge 171 connects hinge member 151 and end 173 of cover plate 107. In one embodiment, only one end of the hinge 151 is a living hinge, preferably the upper end. In another embodiment, both ends of hinge 151 are a living hinge; that is, the hinge is a double hinge. End 173 of cover 106 has an indentation 172 at hinge 171 to prevent the hinge from abutting end 1220 of slot 1214 (FIG. 20). Proximal end 196 of cover plate 107 is preferably radiused. Stop members 131 and 141 are located on base 102 so that the interior walls 137 and 147 of hook-shaped ends 138 and 148 are approximately the same distance apart as the outer edges 181 and 183 of openings 180 and 182.

The structure and chemistry of fluid permeable strip element 160 is known in the art and will not be discussed herein. Preferably, it is an LDL or HDL dry test strip element as described in U.S. patent application Ser. No. 11/207,121 filed Aug. 17, 2005, a glucose dry test strip element, a triglycerides dry test strip element, or a creatinine dry test strip element, though it may be any other dry test strip element known in the art.

Dry strip assembly 100 is assembled by placing a fluid permeable strip element 160 in well 120 and engaging the engagement elements 140 comprising elements 131, 141, 180, 182, 120, and 190 by pressing cover 106 into base 102 so that stop members 131 and 141 pass through openings 180 and 182, respectively, in cover 106. The radius on the distal ends 132 and 142 cause stop members 131 and 141 to bend slightly as cover 106 is pressed into base 102 until lips 134 and 144 pass through openings 180 and 182, respectively. The stop members 131 and 141 then snap back, and lips 134 and 144 latch over edges 181 and 183, respectively, of openings 180 and 182. Thus, the elements 131, 141, 180, and 182 comprise a snap-on latch 188. The step down 119 from platform 114 to platform 111 provides a small amount of leeway so that, if end 199 of cover 106 bends a little under the pressure of closure, it does not interfere with the latching of the stop members.

As cover 106 is closed, compression plate 190 fits into well 120 and compresses dry test strip element 160 against ribs 122 and 124 to form three separate dry test strip test regions 185, 186, and 187 (FIG. 2) that are essentially fluidly isolated from one another. Preferably, these ribs are 0.014 inches and 0.035 inches in height. More preferably, they are between 0.020 inches and 0.030 inches in height. Most preferably, they are 0.025 inches in height. However, the portions of the dry test strip element 160 away from the ribs 122 and 124 are preferably only slightly compressed or, alternatively, uncompressed, so that the carrier does not interfere with free flow of fluid through the test strip test regions 185, 186, and 187. To apply proper pressure to the dry test strip element, the cover 106 and base 102 preferably are made of a material having a greater tensile strength than prior art carriers, preferably between 10,000 pounds per square inch (psi) and 14,000 psi; more preferably, between 11,000 psi and 13,000 psi; and most preferably, 12,000 psi. The preferred material is glass-filled polypropylene, and more preferably with between 20% and 40% glass fill; and most preferably, 30% glass-filled polypropylene. Preferably, the distance between the surface of lips 134 and 144 and the bottom of well 120 is controlled to be just slightly smaller than the distance between the top surface 109 of cover plate 107 at edges 181 and 183 and the bottom surface 193 of compression plate 190 plus the thickness of dry test strip element 160. Alternatively, these distances are set to be essentially equal. In addition, the distance between the surface of landing pads 136 and 146 and the bottom of well 120 is controlled to determine the maximum compression of dry test strip element 160 as the cover is closed. That is, this distance is controlled so that dry test strip element 160 cannot be over compressed so as to damage the dry test strip at ribs 122 and 124 or compact the test strip beyond recovery, which would interfere with the flow of fluid through the strip and decrease accuracy. Thus, the lips 134 and 144 act as a minimum dry test strip compression stop, and the landing pads 136 and 146 act as a maximum dry test strip compression stop.

The compression of the dry test strip 160 preferably also is controlled by adding stiffening ribs 174 and 176 to the cover and stiffening ribs 164 and 165 to the base. The stiffer cover and base reduces inaccuracies in compression due to bending of the plates 104 and 107. It also equalizes the compression in the three test strip test areas 185, 186, and 187.

Figure 4:
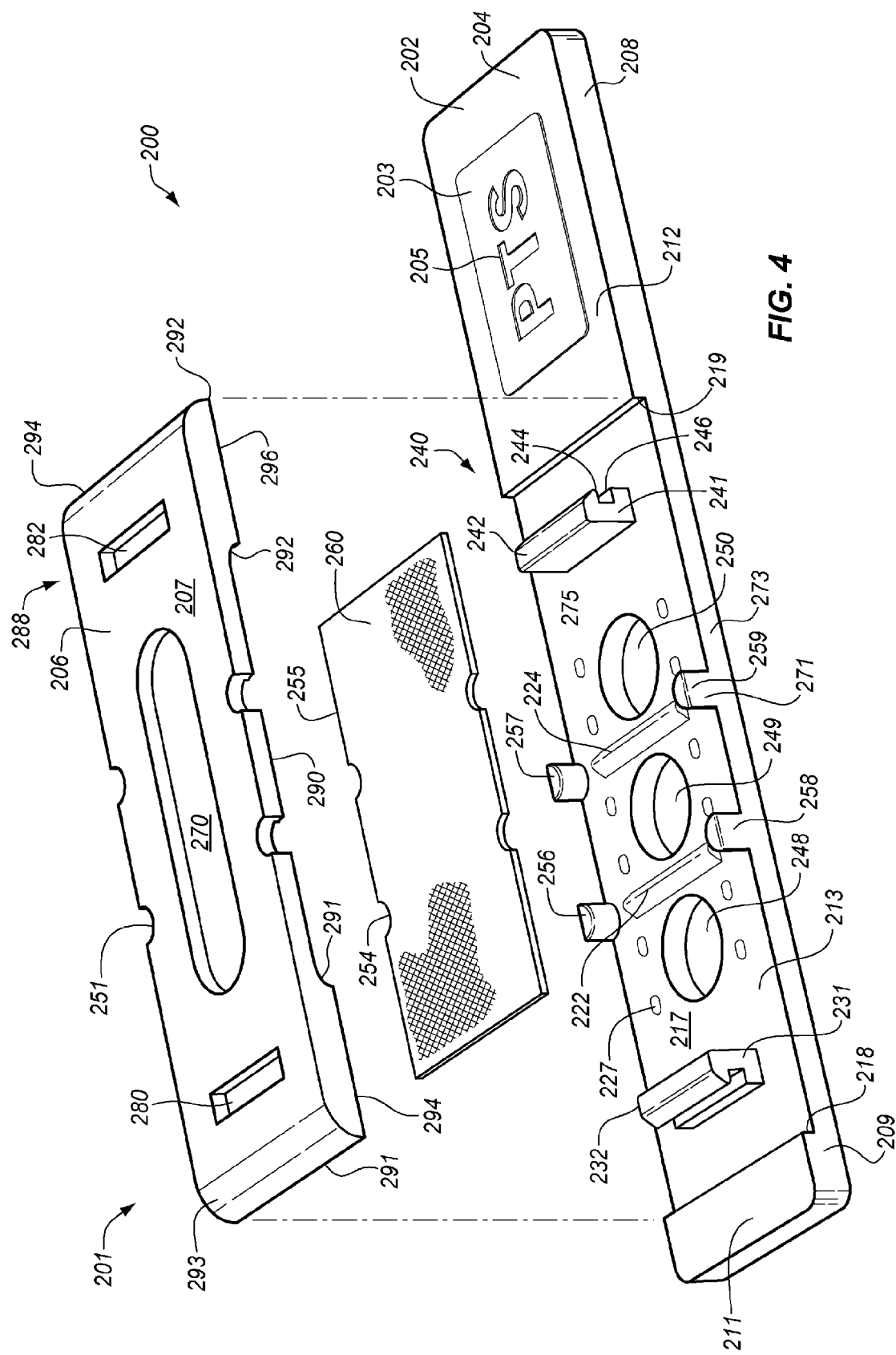
FIG. 4 is an exploded perspective view of another exemplary embodiment of a dry test strip assembly according to the invention.

FIG. 4 shows an exploded perspective view of another preferred embodiment of a dry test strip assembly 200 according to the invention having a proximal end 208 and a distal end 209. Assembly 200 includes carrier 201 and dry test strip element 260. Carrier 201 includes base 202 and cover 206. Base 202 comprises an elongated plate 204 with raised platforms 211 and 212 at the ends and a depressed platform 213 between them. A roughened area 205 is formed on thumb plate 212. Stop members 231 and 241, ribs 222 and 224, and sensor ports 248, 249, and 250 are formed on depressed platform 213 and are as described in the embodiment of FIGS. 1-3. Alignment posts 256, 257, 258, and 259 also are formed on base 202 protruding from depressed platform 213 at its sides. Preferably, the posts are semicircular with a flat surface, such as 271, aligned with the outer edge, such as 273, of the base and a semicircular inner surface, such as 273. Small protrusions such as 227 are formed in the surface 217 of depression 213. These protrusions 227 provide an anti-slip friction surface for dry test strip element 260.

Cover 206 comprises a plate 207 having radiused ends 291 and 292, a recess 290, a sample port 270, openings 280 and 282 for receiving stop members 231 and 241, respectively, and guide grooves, such as 251, which are preferably semicircular. The end walls 291 and 292 of recess 290 are radiused. Recess 290 is essentially the size and shape of dry test strip element 260.

Dry test strip element 260 is as discussed above, except that semicircular guide indentations, such as 254, are formed in the longitudinal edges, such as 255.

Dry test strip assembly 200 preferably IS assembled by engaging the engagement elements. Engagement elements 240 comprise elements 231, 241, 280, 282, and 256-259, while snap-on latch 242 comprises elements 231, 241, 280, and 282. The elements are engaged by placing dry test strip element 260 on surface 217 of depression 213 with indentations 254 fitting on guide posts 256-258. Cover 206 then is placed over base 202 with guide grooves 251 fitting over guide posts 256-258, dry test strip 260 fitting into recess 290, stop members 232 and 242 snapping into openings 280 and 282, respectively, as described in reference to the embodiment of FIGS. 1-3, and ends 291 and 292 of cover 206 abutting the end walls 218 and 219, respectively, of depression 213. The lower surfaces 294 and 296 of cover 206 rest on surface 217 of depression 213. As in the embodiment of FIGS. 1-3, lips 231 and 244 act as a minimum dry test strip compression stop, and landing pads 232 and 246 act as a maximum dry test strip compression stop.

Figure 5:
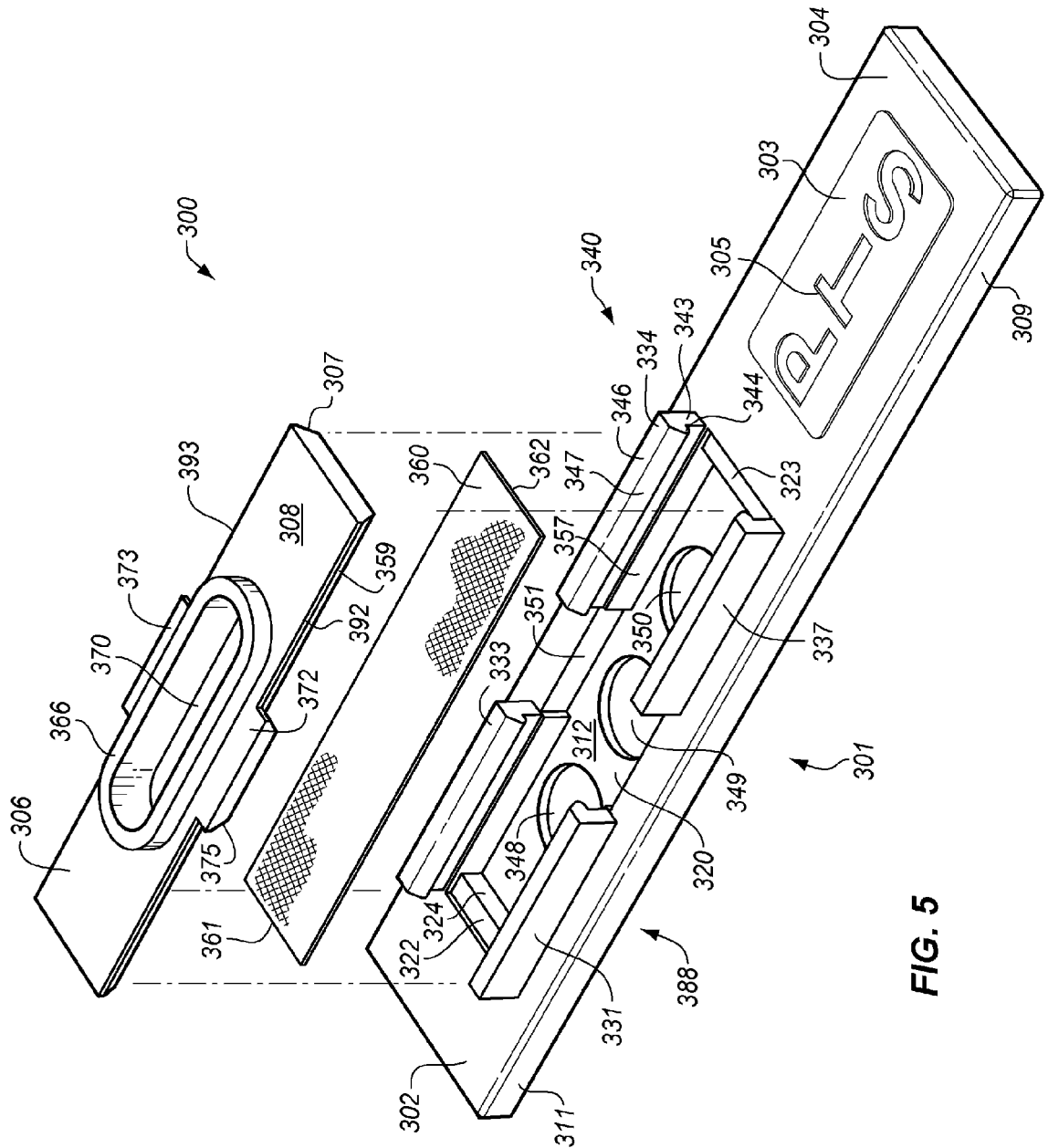
FIG. 5 is an exploded perspective view of another exemplary embodiment of a dry test strip assembly according to the invention.

FIGS. 5-11 illustrate another preferred embodiment of a dry test strip assembly 300 according to the invention, this embodiment having a proximal end 309 and a distal end 311. Dry test strip assembly 300 includes test strip carrier 301 and dry test strip element 360. Test strip carrier 301 includes base 302 and cover 306. FIG. 5 is an exploded perspective view of assembly 300, FIG. 6 is a top plan view of the base 302 of the carrier, FIG. 7 is a cross-section view of the base 302 taken through the line 7-7 of FIG. 6, FIG. 8 is a cross-section view of the base 302 taken through the line 8-8 of FIG. 6, FIG. 9 is a top plan view of the cover 306 of the carrier, FIG. 10 is a side view of the cover 306; and FIG. 11 is an end view of the cover 306.

Base 302 comprises an elongated plate 304, again with a thumb plate 303 having a roughened area 305. A well 320 is formed in plate 304, and three sensor ports 348, 349, and 350 are formed in the bottom 317 of well 320. Cover landing pads 322 and 323 are formed at the proximal and distal ends of well 320. Rectangular grooves 351 and 352 are formed along the sides 356 and 357 of well 320 in the center portion of the well. Stop members 331, 337, 333, and 334 extend upward from plate 304 aligned with the sides 356 and 357 of well 320. Each stop member, such as 334, includes a vertical pillar, such as 343, at the top of which is a hook-shaped latch member having a ramp 347 and a lip 344. Dry test strip element 360 is as discussed above.

Cover 306 comprises a plate 308 having a sample opening 370. The shape and dimensions of the opening 370 is as described in reference to the openings 170 and 270 of the previous embodiments. However, in the vertical direction, a rib 366 extends vertically from plate 308 and encircles opening 270. Guide members 372 and 373 extend horizontally from the side plate 307, preferably in the center of the elongated length. Each guide member has ramps 375 sloping at an angle to the vertical in a plane perpendicular to the vertical. The longitudinal sides of plate 307 form ramps 359 along the elongated direction.

Dry test strip assembly 301 is assembled by placing dry test strip element 360 in well 320 with its ends 361 and 362 abutting end walls 324 and 325, respectively, of well 320. As will be seen below, dry test strip 360 comprises a multilayered structure including a plurality of membranes. The membranes can either be stacked separately in well 320, or more than one membrane at a time can be placed in well 360. Cover 306 then is placed over base 302 with guide members 372 and 383 aligned over grooves 351 and 352, respectively. Cover 306 then is pressed into base 302 with ramps 375 of guide members 372 and 373 riding on the sides of grooves 351 and 352, ramps 347 of stop members 331-334 riding on ramps 359 of cover plate 306 until the edges 392 and 393 of cover plate 306 snap under lips 344 of stop members 331-334 and the bottom surface 397 of plate 306 at ends 394 and 395 rests on the upper surfaces of cover landing pads 322 and 323. The compression of dry test strip element 360 in well 320 is controlled by cover landing pads 322 and 324 and lips 344, with lips 344 acting as a minimum dry test strip compression stop and the cover landing pads 322 and 324 acting as a maximum dry test strip compression stop. Rib 366 stiffens the cover in the critical central area assisting in controlling compression and equalizing the compression over the three sensor ports 348-350. Similarly, stop members 331-334 stiffen the base 301. In this embodiment, the engagement elements 340 include elements 331, 337, 333, 334, 359, 392, 393, 372, 373, 351, 352, 322, and 323; and the snap-on latch includes elements 331, 337, 333, 334, 359, 392, and 393.

Figure 13:
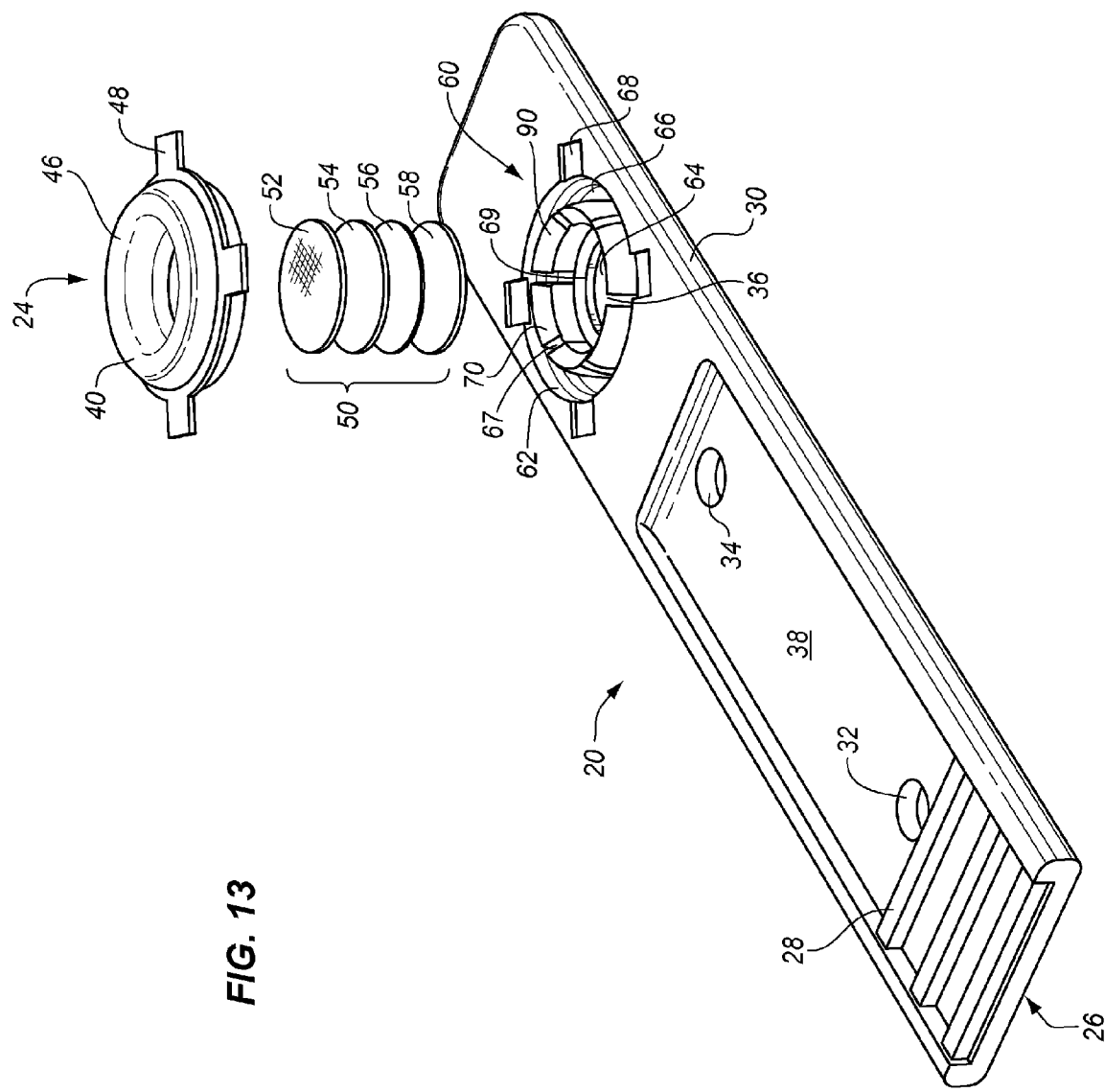
FIG. 13 is an exploded perspective view of the test strip assembly of FIG. 12.

Another exemplary embodiment of a dry test strip assembly 20 according to the invention is shown in FIGS. 12-19. An exploded perspective view of the test strip assembly 20 is shown in FIG. 13. Test strip assembly 20 includes a preferably elongated test strip carrier body 30, a test strip element 50, and a test strip carrier 24. Test strip carrier 24 includes a carrier base portion 60 and a carrier cap 40. Carrier body 30 includes a grip portion 26, openings 32 and 34, sensor port or test opening 36, and carrier base 60. Grip portion 26 includes raised ribs 28, which permit the fingers to easily grip the carrier body 30.

Figure 14:
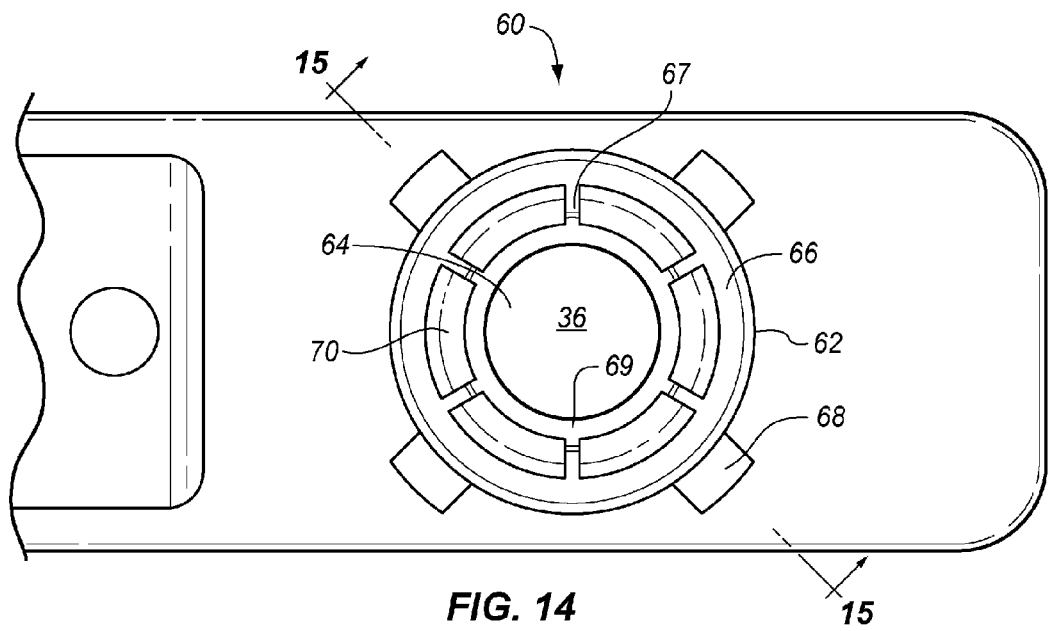
FIG. 14 is a top view of a portion of the base portion of the test strip assembly of FIG. 12.
Figure 15:
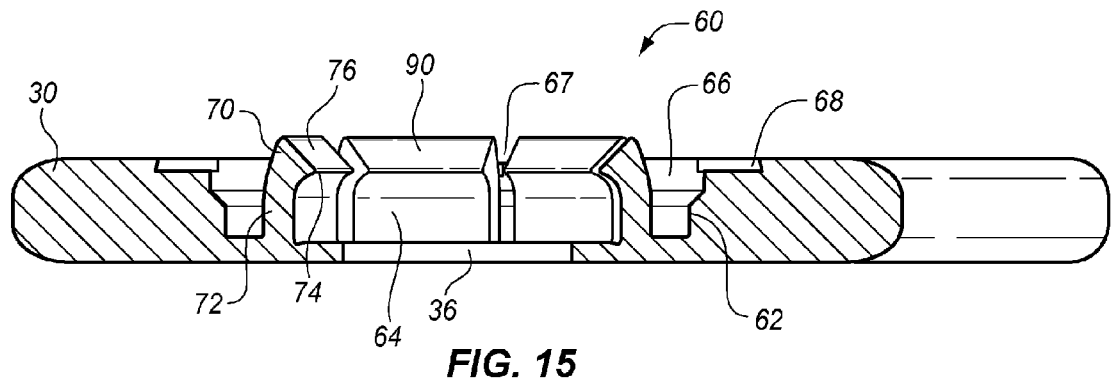
FIG. 15 is a cross-sectional view of the base portion of the test strip assembly of FIG. 2 taken through the line 15-15 of FIG. 14.
Figure 19:
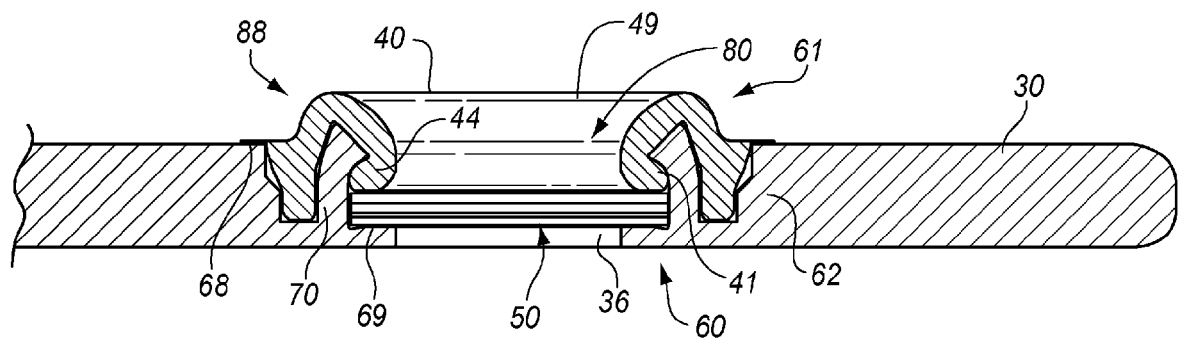
FIG. 19 is a cross-sectional view of the assembled test strip assembly of FIG. 12 taken through the line 19-19 of FIG. 12.

The carrier base 60 is shown in FIGS. 13, 14, 15, and 19. FIG. 13 shows a perspective view, FIG. 14 shows a top view, FIG. 15 shows a cross-sectional view through lines 5-5 in FIG. 14, and FIG. 19 shows the cap 40 in place over carrier base 60. Preferably, carrier base 60 includes a well 62 formed in body 30, alignment recesses 68, and retainer 90, which is preferably flexible. Well 62 has an upward sloping well wall 83 completely encircling the test opening (sensor port) 36. Retainer 90 preferably comprises fingers 70 and separates well 62 into an inner portion 64, which forms a test strip well 62, and an outer portion 66, which is preferably relatively small in volume, being just big enough to allow fingers 70 to flex. In this disclosure, the term "encircle" does not necessarily mean the encircling structure forms a circle, but rather it has the broader common meaning of "to pass completely around". In the preferred embodiment, however, the well 62 and fingers 70 do form a circle. In the preferred embodiment, there are four alignment recesses 68 and six fingers 70, though the invention contemplates that any number suitable to perform the functions described below may be used. Each finger 70 includes a stem portion 72, a hook portion 74, and a ramp portion 76 that preferably is formed at an acute angle to a vertical line perpendicular to the plan of body 30. Fingers 70 are separated by channels 67. The bottom of well 62 forms a test strip support 69 around port 36 on which, as will be seen below, the test strip element 50 rests, as best shown in FIG. 9.

Figure 16:
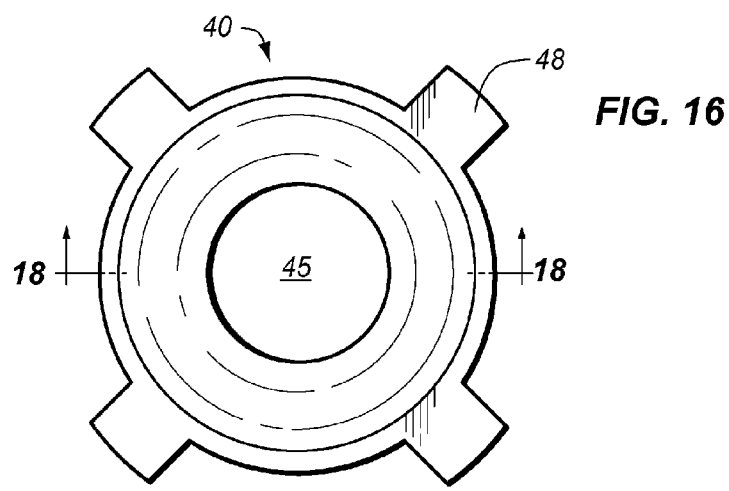
FIG. 16 is a top plan view of the cap portion of the test strip assembly of FIG. 12.
Figure 17:
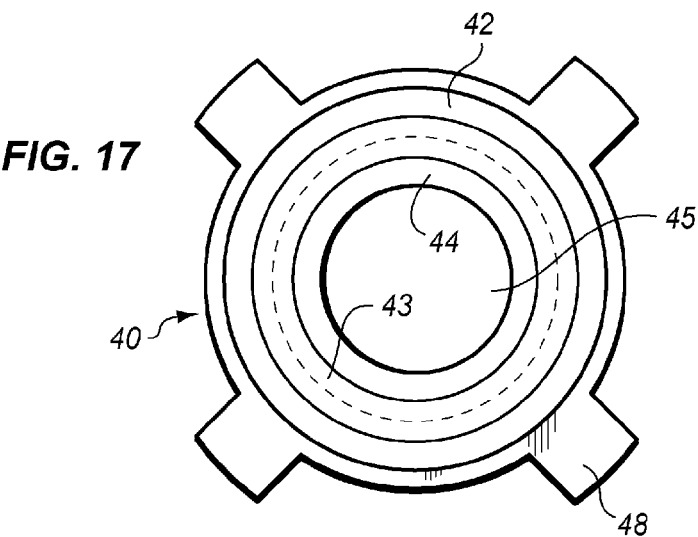
FIG. 17 is a bottom plan view of the cap portion of the test strip assembly of FIG. 12.
Figure 18:
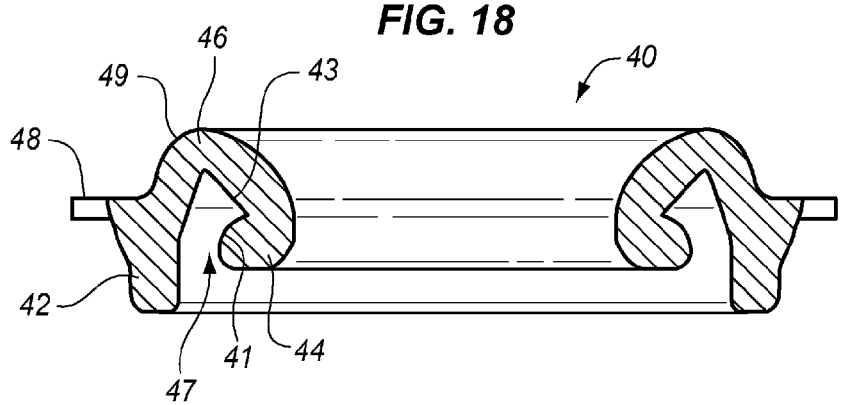
FIG. 18 is a cross-sectional view of the cap of FIG. 6 taken through the line 18-18 of FIG. 16.

Cap 40 is shown in FIGS. 13 and 16-19. FIG. 13 shows a perspective view, FIG. 16 shows a top plan view, FIG. 17 shows a bottom plan view, FIG. 18 shows a cross-sectional view through line 18-18 of FIG. 16, and FIG. 19 shows a cross-sectional view of the cap 40 in place over the carrier base 60. Cap 40 includes an outer foot 42, an inner flange 44, and a connecting portion 46, which, as will be seen below, forms the brim 49 of a bodily fluid container 80. The outer foot 42 and inner flange 44 have different lengths, with the inner flange 44 being shorter. The difference in lengths is less than the thickness of test strip assembly 50, so that the inner flange 44 and test strip support 69 engage strip 50 sufficiently to secure it in place. Preferably, the difference is sufficient so that the inner flange 44 and test strip support 69 compress strip element 50 between them. The bottom 43 of connecting portion 46 is shaped to form a groove 47 into which fingers 70 fit snuggly. A lip 41 is formed on inner flange 44 (FIGS. 18 and 19) which engages hook 74 to latch cap 40 on carrier base 60. The distal end 84 of inner flange 44 is smooth and rounded so as not to damage test strip element 50.

Test strip 50 is shown in FIGS. 13 and 19, and preferably is formed of a plurality of layers. Each layer performs a specific function as required by each specific test. Generally, there is a "spreading" or "disbursement" layer 52 to ensure even distribution of the whole blood sample; a "separation" layer 54 to obtain a clarified plasma/serum sample; a layer or layers 56 to hold specific test reagents in sequence as needed by each specific assay; and a final "color" or "test reaction" layer 58 to provide a matrix on which a specific color or test reaction will develop for each specific test. The order of the layers can vary. For example, the separation layer may come before or after the reagent layer(s). The details of the test strip layers are described in U.S. patent application Ser. No. 11/207,121 filed Aug. 17, 2005, which is incorporated by reference to the same extent as though fully disclosed herein. Together, the layers 54, 56, and 58 shall be referred to as "reagent layers", because they typically include reagents, to distinguish them from disbursement layer 52. The test strip elements 160, 260, and 360 of the previous embodiments are made in a similar fashion, except for the fact that they are differently shaped and, in the regions above the separate test ports, such as in each of the separate fluid tight compartments of the embodiments of FIGS. 1-4, they contain different reagents.

The test strip assembly 20 is assembled as shown in FIGS. 13 and 19. As will be described in more detail below in relation to FIG. 21, a cone-shaped inserter (FIG. 21) presses down on the ramps 76 of the fingers 70 and spreads them sufficiently to drop the assembled test strip 50 onto test strip support 69. Cap 40 then is pressed home on retainer 90, with fingers 70 forced into groove 47, compressing test strip 50 sufficiently to hold it in place. In this embodiment, engagement elements 61 include elements 48, 68, 62, 42, and 70; and snap-on latch 88 includes elements 41 and 74.

FIG. 20 shows a photometric analyzer 1210 according to the preferred embodiment of the invention. The photometric device includes a housing 1212 that is sized and configured to be easily hand-held. The housing defines a dry test strip assembly holding slot 1214 that receives a test assembly, such as the assemblies 100, 200, 300, and 20 shown in FIGS. 1-19. A number of analyzer sensor ports 1215, 1216, and 1217 are spaced in slot 1214 to correspond to the spacing of sensor ports, such as 148, 149, and 150 in the test strip assemblies. Light sources and light sensors integrated into the device 1210 interact, via the sensor ports, with the test strip, such as 160 (FIGS. 1-3) in the dry strip test assemblies, such as 100. A display 1218 provides a visual and/or numeric read-out indicative of the concentration or other parameter of a particular analyte being evaluated. The device 1210 includes circuitry and a microprocessor configured to analyze the colorimetric response of the reacted test strip according to known techniques. The preferred photometric device 1210 and its operation is more fully described in U.S. Pat. No. 5,597,532 and, thus, will not be described in detail herein. In the preferred embodiment, the device 1210 is the same as the device described in the foregoing patent, except that the device is designed and programmed to operate with the test assemblies 100, 200, and 300 according to the invention. However, any device that has the ability to determine the intensity of light, the frequency or wavelength of light, or other property of light reflecting, scattered, or otherwise interacting with the test strip assemblies according to the invention, may be used.

Figure 21:
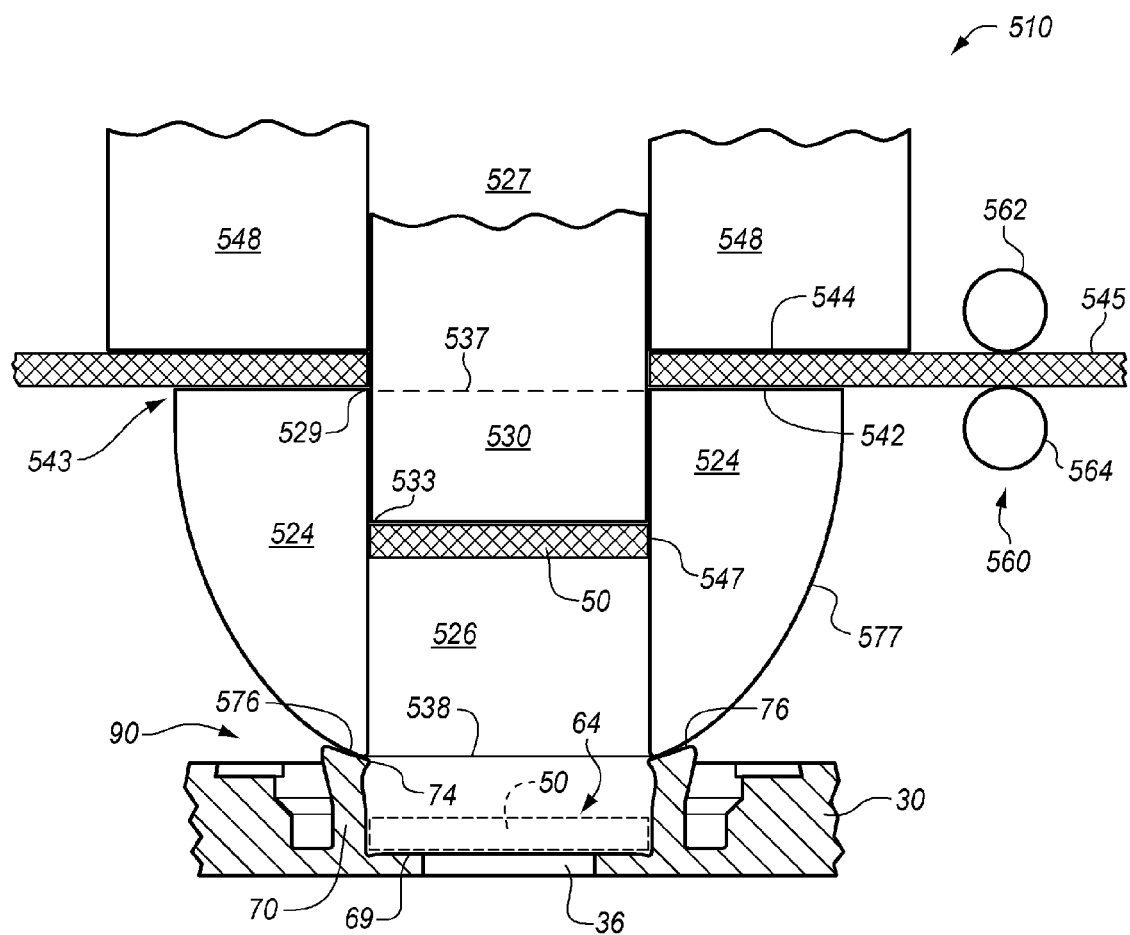
FIG. 21 is a plan view illustrating a portion of an exemplary manufacturing process and manufacturing apparatus according to the invention.

The test assembly 20 is assembled as shown in FIGS. 13, 19, and 21. The test element cutting and insertion system 510 is shown in FIG. 21. Cutting and insertion system 510 includes a die/inserter 524, a punch 530, a punch guide 548, and a test strip material drive mechanism 560. A sheet or ribbon 545 of test strip material is also shown in FIG. 21. The sheet or ribbon 545 of test strip material preferably is multi-layered as shown at 50 in FIGS. 13 and 19. The die/inserter 524 has channel 526 passing through the die, a cutting edge 529 formed about the perimeter of the proximal end 537 of the channel, and a ramped surface 576 about the periphery of the distal end 538 of the channel. The cutting edge 529 is substantially shaped in the form of the desired outer perimeter 547 of a test strip element 50. The upper surface 542 of die/inserter 524 preferably is flat and provides a support and guide for test sheet or ribbon 545. Preferably, the outer surface 577 of the die/inserter is cone-shaped. Test sheet or ribbon drive mechanism 560 preferably comprises a first roller 562 and a second roller 564 that rotate in opposite directions to move sheet or ribbon through guide slot 543. Punch guide 548 includes a bore 527 in which the punch slides. The lower surface 544 of guide 548 preferably is flat and forms the upper guide for test sheet or ribbon 545. Punch 530 is sized and shaped to slide snuggly in channel 526. The punch 530 has a cutting edge 533 formed about the perimeter of punch 530.

The manufacturing process is as follows. Cutting and inserting assembly 510 is located above the test port 36 in test strip carrier body 30, preferably by moving an injection molded test strip carrier assembly having a plurality of test strip carrier bodies 30 into place below the inserter and under the distal end 538 of die/inserter 524. However, this could also be done by moving the cutting and inserting assembly 510. Punch 530 is driven downward into contact with sheet or ribbon 545. Punch edge 533 cooperates with the die edge 529 to cut out a test element 50. Punch 530 continues to be driven downward, pushing test element 50 through die channel 526 and out its distal end 538. Meanwhile, cone-shaped inserter 524 is driven downward so that ramp surface 576 presses against the ramps 76 of the fingers 70 and spreads them sufficiently to drop the assembled test strip element 50 onto test strip support 69. The punch and die/inserter 524 then retreats upward, and carrier body 30 moves to a different assembly station where cap 40 then is pressed home on retainer 90, with fingers 70 forced into groove 47, compressing test strip element 50 sufficiently to hold it in place.

Figure 22:
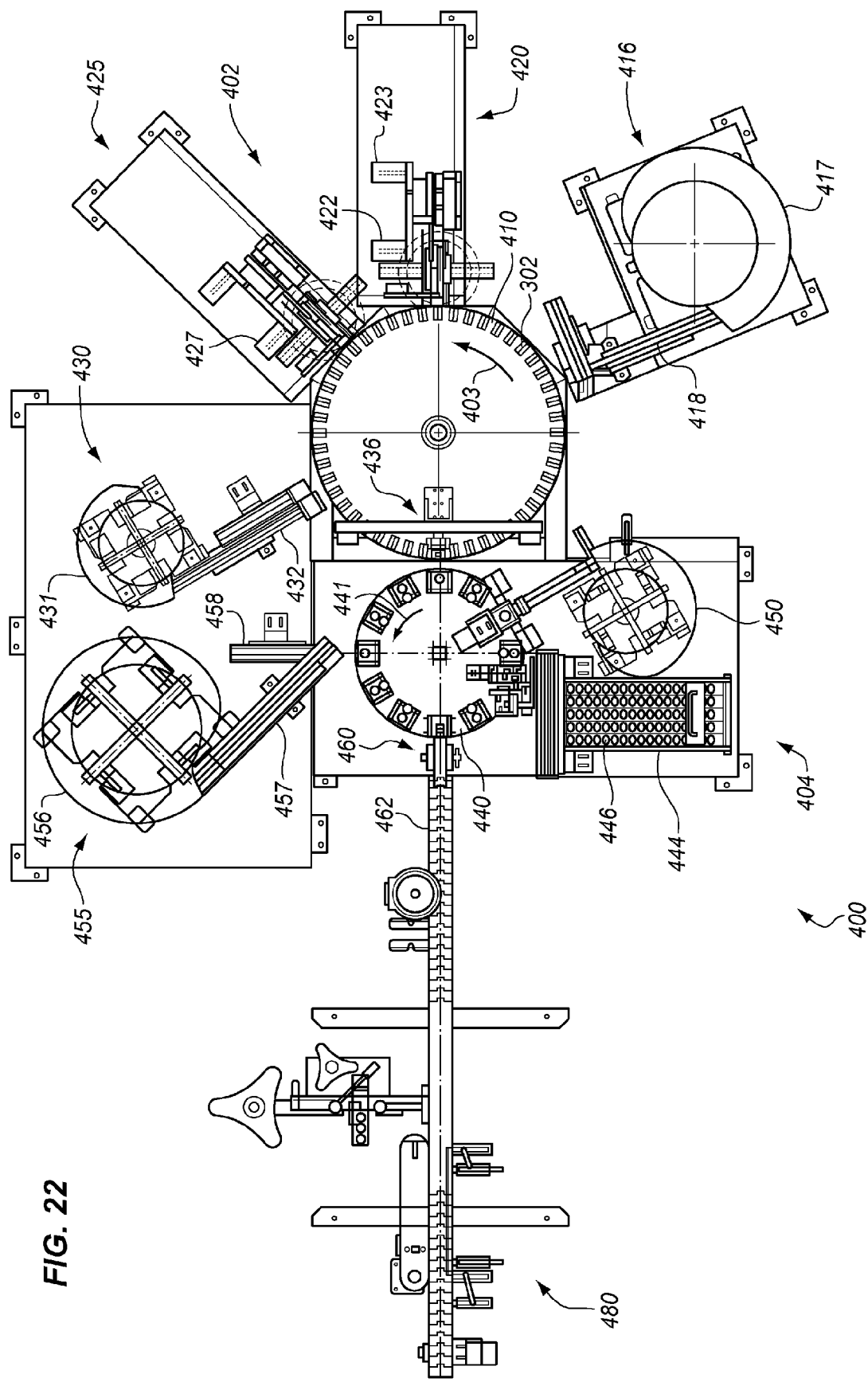
FIG. 22 is a plan overhead view showing the system and process for manufacturing the test strip assembly of FIGS. 5-11.

FIG. 22 is a plan overhead view showing the system 400 and process for manufacturing the test strip assembly of FIGS. 5-11. Dry test strip assembly manufacturing system 400 comprises a dry test strip assembly assembler 402 and vial loading system 404. Assembler 402 comprises an assembler dial 410, strip carrier base feeder bowl station 416, layered membrane cut and place station 420, disbursement membrane cut and place station 425, strip carrier cover feeder bowl station 430, and assembled strip transfer station 440. Vial loading system 404 comprises vial loading dial 440, vial tray station 444, desiccant feeder bowl station 450, assembled strip loading station 436, vial capping station 455, vial transfer station 460, and vial labeler 480.

The operation of the manufacturing system 400 can be understood in conjunction with FIGS. 22 and 5. Assembler dial 410 turns in the direction of arrow 403 while vial loading dial 440 turns in the direction of arrow 441. At strip carrier base feeder bowl station 416, a vibrating bowl 417 isolates individual dry test strip bases 302 and places them on conveyer 418, which then places them on assembler dial 410 where they are carried to layered membrane cut and place station 420. Station 420 includes a roll 422 of membrane ribbon that includes the reagent layers, i.e., the layers corresponding to layers 54, 56, and 58 in the embodiment of FIG. 13. This roll can be prepared separately. Alternatively, a plurality of rolls 422, 423, each including a ribbon of membrane corresponding to one of the three layers, may be unwound simultaneously. A shear cuts a piece off the end of the ribbon and station 420 deposits it in well 320. The base 302 with the multilayered membrane is carried by dial 410 to disbursement membrane station 425. Station 425 includes a roll 427 of a ribbon of a disbursement membrane, corresponding to membrane 52 of FIG. 13. At station 425, the end of the ribbon is sheared off and placed on top of the multilayered membrane in well 320. Dial 410 then carries the base 302 with the stack of membranes to station 430. At station 430, a vibrating bowl 431 isolates individual covers 306 and places them on conveyer 432 which carries them to dial 410 where they are placed on and pressed into base 302. This completes the assembly of the test strip assembly 300, which is then carried by dial 410 to transfer station 436 where the assemblies are counted and loaded into a vial as discussed below.

At station 444, vials 446 are placed on dial 440. Dial 440 carries the vial to assembled strip loading station 436, where the completed dry test drip assembles 300 are deposited into the vial. Dial 440 then carries the loaded vial to vial capping station 455 which includes a vibrating bowl 456. Vibrating bowl 456 isolates individual caps and places then on conveyer 457 where they are conveyed to cap applicator 458 which snaps them onto the individual vials. At vial transfer station 460, the vials are transferred to conveyer 462 of labeler 480. The vials then are labeled with a label providing time and date, the type of strip and the batch of each of the strips, and other details of the particular run. Labeler 480 is a model Econoline labeler made by Quadrel Labeling Systems, Inc. 7670 Jenther Drive, Mentor, Ohio 44060.

A feature of the invention is the snap-on cover. This makes it easier to assemble the dry test strip assembly without human handling. A related feature is that the design of the stops allows a dry test strip assembly to be assembled automatically by machines and still provide a compression of the test strip element that provides more accurate analysis. A further related feature is that the design, such as the stiffness of the material of which the carrier is made, permits the compression to be uniform across a multi-test strip with multiple test ports.

Another feature of the invention is the ribs 222 and 224 in the embodiments of FIGS. 1-4. This, with assistance from the controlled compression, allows the strip elements 160, 260 to be separated into a plurality of fluid-tight compartments, and at the same time permitting a multi-analyte dry test strip assembly to be made with a single continuous strip element 160. The fluid-tight compartments are the portions of the test strip element above each of the ports 148, 149, and 150 in FIGS. 1-3 and ports 248, 249, and 250 in FIG. 4. In the prior art, such multi-analyte strip assemblies were made with breaks in at least the reagent layers between the different portions of the strip above the separate test ports. These breaks essentially created separate stacks of layers. This required the reagent layers to be separately placed above each test port or the separated reagent layers to be glued to a disbursement layer, either of which made assembly by machine impossible.

There has been described a novel dry test strip system that enhances the accuracy of the dry test strip as well as makes it easier to assemble with machinery. It should be understood that the particular embodiments shown in the drawings and described within this specification are for purposes of example and should not be construed to limit the invention, which will be described in the claims below. Further, it is evident that those skilled in the art may now make numerous uses and modifications of the specific embodiments described, without departing from the inventive concepts. For example, while the ports in the test strips have been shown as circular, other shapes may also be used. It is also evident that the methods recited may in many instances be performed in a different order; or equivalent structures and processes may be substituted for the various structures and processes described. Consequently, the invention is to be construed as embracing each and every novel feature and novel combination of features present in and/or possessed by the bodily fluid analysis system herein described.

What is claimed as new and desired to be protected by Letters Patent of the United States is:

1. A carrier system for a diagnostic dry test strip for use in measuring an analyte in a fluid sample, said carrier system comprising:

a carrier base including a test strip well configured to receive a dry test strip and a test port communicating with said well and enabling said test strip to be observed;

a cover having a sample opening; and engagement elements on said carrier base and said cover configured to engage said cover to said carrier base with said sample opening aligned over said test port and said dry test strip compressed between said carrier base and said cover;

wherein said engagement elements include: a maximum dry test strip compression stop controlling the maximum compression on said dry test strip; and a minimum dry test strip compression stop controlling the minimum compression on said dry test strip, the engagement elements including a stop member, the minimum dry test strip compression stop being a lip that extends from an end of the stop member, the maximum dry test strip compression stop being a landing pad that extends from the stop member, the minimum dry test strip compression stop and maximum dry test strip compression stop being separated on the stop member such that they form a hook-shaped end, wherein the engagement elements include an attachment opening, the opening including an edge that engages the hook-shaped end between the lip and the landing pad.

\* \* \* \* \*